(12) United States Patent
Lin et al.

(10) Patent No.: US 7,804,938 B2
(45) Date of Patent: Sep. 28, 2010

(54) X-RAY IMAGING APPARATUS AND FLUOROSCOPIC IMAGE DISPLAY APPARATUS

(75) Inventors: Mei Lin, Beijing (CN); Huanzhong Li, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 12/339,659

(22) Filed: Dec. 19, 2008

(65) Prior Publication Data

US 2009/0168956 A1    Jul. 2, 2009

(30) Foreign Application Priority Data

Dec. 28, 2007    (CN) .................... 2007 1 0144185

(51) Int. Cl.
    *H05G 1/28* (2006.01)
(52) U.S. Cl. ........................ 378/165; 378/98.5
(58) Field of Classification Search ............. 378/44, 378/62, 98.5, 98.9, 162–165
    See application file for complete search history.

(56) References Cited

U.S. PATENT DOCUMENTS

| | | | |
|---|---|---|---|
| 4,274,006 A | 6/1981 | Caine | 378/165 |
| 4,429,412 A | 1/1984 | Pierce et al. | 378/165 |
| 5,189,690 A | 2/1993 | Samuel | 378/162 |
| 5,193,106 A | 3/1993 | DeSena | 378/163 |
| 5,345,494 A | 9/1994 | Willey | 378/162 |
| 6,097,978 A | 8/2000 | Demarais et al. | 600/429 |
| 6,160,870 A | 12/2000 | Jacobson | 378/165 |
| 7,123,690 B1 | 10/2006 | Brown et al. | 378/165 |
| 2007/0286341 A1* | 12/2007 | Kamegawa et al. | 378/63 |

FOREIGN PATENT DOCUMENTS

JP    2001-243448    9/2001

* cited by examiner

*Primary Examiner*—Courtney Thomas
(74) *Attorney, Agent, or Firm*—Armstrong Teasdale LLP

(57) ABSTRACT

An X-ray imaging apparatus and a fluoroscopic image display apparatus are provided for displaying postural information of a subject on a fluoroscopic image. The X-ray imaging apparatus detects an X-ray irradiated from an X-ray irradiator and passing through a subject and takes a fluoroscopic image. The X-ray detector includes a visible indicator at a corner of an X-ray incidence plane, a display device that displays a fluoroscopic image based on a detection signal from the X-ray detector together with an orient mark corresponding to the indicator, and a writing device that enables a mark indicating the posture of a subject on the displayed fluoroscopic image.

20 Claims, 9 Drawing Sheets

X-RAY IMAGING APPARATUS AND FLUOROSCOPIC IMAGE DISPLAY APPARATUS

CROSS REFERENCE TO RELATED APPLICATIONS

This application claims the benefit of Chinese Patent Application No. 200710144185.3 filed Dec. 28, 2007, which is hereby incorporated by reference in its entirety.

BACKGROUND OF THE INVENTION

The subject matter disclosed herein relates to an X-ray imaging apparatus and a fluoroscopic image display apparatus, and specifically relates to an X-ray imaging apparatus that detects X-rays irradiated from an X-ray irradiator, passed through a subject, and takes a fluoroscopic image, and an apparatus to display that fluoroscopic image.

An X-ray imaging apparatus irradiates X-rays to a subject from an X-ray irradiator, and detects transmitted X-rays with an X-ray detector to form a fluoroscopic image. The subject faces the X-ray detector between the X-ray irradiator and the X-ray detector in a lying posture.

There are two postures of the subject facing the X-ray irradiator; a posture in which the belly of the subject faces the X-ray irradiator and that in which the back the subject faces the X-ray irradiator. The fluoroscopic images taken in these different postures are reversed in left-right direction. Therefore, the fluoroscopic image is analyzed to determine the posture, and the result is displayed on the fluoroscopic image (refer to Japanese Unexamined Patent Publication No. 2001-243448), as an example).

BRIEF DESCRIPTION OF THE INVENTION

In order to determine the posture correctly from a fluoroscopic image, advanced image analytical capability is required. Accordingly, it is not practical to provide such a capability to a middle-end or low-end X-ray imaging apparatus, apart from a high-end X-ray imaging apparatus.

Therefore, the embodiments described herein provide an X-ray imaging apparatus and a fluoroscopic image display apparatus that allows easy acquisition of postural information on the subject from displayed fluoroscopic images.

The first aspect of the invention to solve the problem is an X-ray imaging apparatus that detects X-rays irradiated from an X-ray irradiator and passed through a subject to take fluoroscopic images, the X-ray imaging apparatus comprising: the X-ray irradiator; an X-ray detector having an visible indicator at the end of the X-ray incidence plane as the positional standard on the X-ray incidence plane; and a display device that displays fluoroscopic images based on the detection signals from the X-ray detector together with an orient mark corresponding to the position of the indicator described above.

The second aspect of the invention to solve the problem is an X-ray imaging apparatus described in the first aspect, wherein the X-ray detector has the indicator on either side of the approximately line symmetrical subject, and the display device displays the orient mark on the side corresponding to the indicator for the symmetrical image of the approximately line symmetrical subject.

The third aspect of the invention to solve the problem is an X-ray imaging apparatus described in the second aspect, wherein the display device displays the orient mark on left or right side of the human subject.

The fourth aspect of the invention to solve the problem is an X-ray imaging apparatus described in the first or third aspect, further comprising a writing device that enables a mark indicating the direction of the subject to be written on a fluoroscopic image displayed by the display device.

The fifth aspect of the invention to solve the problem is an X-ray imaging apparatus described in the fourth aspect, wherein the X-ray detector has the indicator on either side of the approximately line symmetrical subject; the display device displays the orient mark on side corresponding to the indicator for the approximately line symmetrical subject; and the writing device enables the mark indicating the direction of the subject to be written on the same side as the orient mark.

The sixth aspect of the invention to solve the problem is an X-ray imaging apparatus described in the fifth aspect, wherein the display device displays the orient mark on left or right of the human subject, and the writhing device enables a mark indicating whether the direction of the subject is right or left to be written on the same side as the orient mark.

The seventh aspect of the invention to solve the problem is an X-ray imaging apparatus described in the first aspect, wherein the indicator is an indicator of X-ray permeability.

The eighth aspect of the invention to solve the problem is an X-ray imaging apparatus described in the first aspect, wherein the display apparatus that enables the fluoroscopic image to be displayed reversely by rotating or flipping the fluoroscopic image.

The ninth aspect of the invention to solve the problem is an X-ray imaging apparatus described in the eighth aspect, wherein the display apparatus displays the indicator in a constant direction.

The tenth aspect of the invention to solve the problem is an X-ray imaging apparatus described in the eighth or ninth aspect, wherein the display apparatus displays the orient mark in a constant direction.

The eleventh aspect of the invention to solve the problem is a fluoroscopic image display apparatus that displays a fluoroscopic image of a subject taken by an X-ray imaging apparatus, comprising a display device that displays the fluoroscopic image together with an orient mark which is provided at the end of the X-ray incidence plane of the X-ray detector used for taking the fluoroscopic image, and which corresponds to the visible position as the positional standard on the X-ray incidence plane.

The twelfth aspect of the invention to solve the problem is a fluoroscopic image display apparatus described in the eleventh aspect, wherein the display device displays the orient mark on the side corresponding to the indicator for the symmetrical image of the approximately line symmetrical subject.

The thirteenth aspect of the invention to solve the problem is a fluoroscopic image display apparatus described in the twelfth aspect, wherein the display device displays the orient mark on the left or right of the human subject.

The fourteenth aspect of the invention to solve the problem is a transmission display apparatus described in the twelfth aspect, wherein the fluoroscopic image display apparatus is equipped with a writing device that enables a mark indicating the direction of the subject on a fluoroscopic image displayed by the display device.

The fifteenth aspect of the invention to solve the problem is a fluoroscopic image display apparatus described in the fourteenth aspect, wherein the display device displays on the side corresponding to the indicator for the symmetrical image of the approximately line symmetrical subject, and the writing device enables the mark indicating the direction of the subject on the same side as the orient mark.

The sixteenth aspect of the invention to solve the problem is a fluoroscopic image display apparatus described in the fifteenth aspect, wherein the display device displays the orient mark on the left or right of the human subject, and the writing device enables a mark indicating whether the direction of the subject is right or left to be written on the same side as the orient mark.

The seventeenth aspect of the invention to solve the problem is a fluoroscopic image display apparatus described in the eleventh aspect, wherein the display device can change the direction of the fluoroscopic image by rotating or reversing the fluoroscopic image.

The eighteenth aspect of the invention to solve the problem is a fluoroscopic image display apparatus described in the seventeenth aspect, wherein the display apparatus displays the indicator in a constant direction.

The nineteenth aspect of the invention to solve the problem is a fluoroscopic image display apparatus described in the seventeenth or eighteenth aspect, wherein the display apparatus displays the orient mark in a constant direction.

According to the invention, the X-ray imaging apparatus and the fluoroscopic image display apparatus is an X-ray imaging apparatus that detects, with an X-ray detector, X-rays irradiated from an X-ray irradiator and passed through a subject, the X-ray imaging apparatus comprising: an X-ray detector with a visible indicator at one end of the X-ray incidence plane; a display device that displays the fluoroscopic image based on the detected signal from the X-ray detector together with an orient mark corresponding to the indicator; and a writing device that enables a mark indicating the posture of a subject on the displayed fluoroscopic image. Therefore, it is possible to easily obtain the postural information of a subject from the displayed fluoroscopic image.

DETAILED DESCRIPTION OF THE INVENTION

Figure 1:
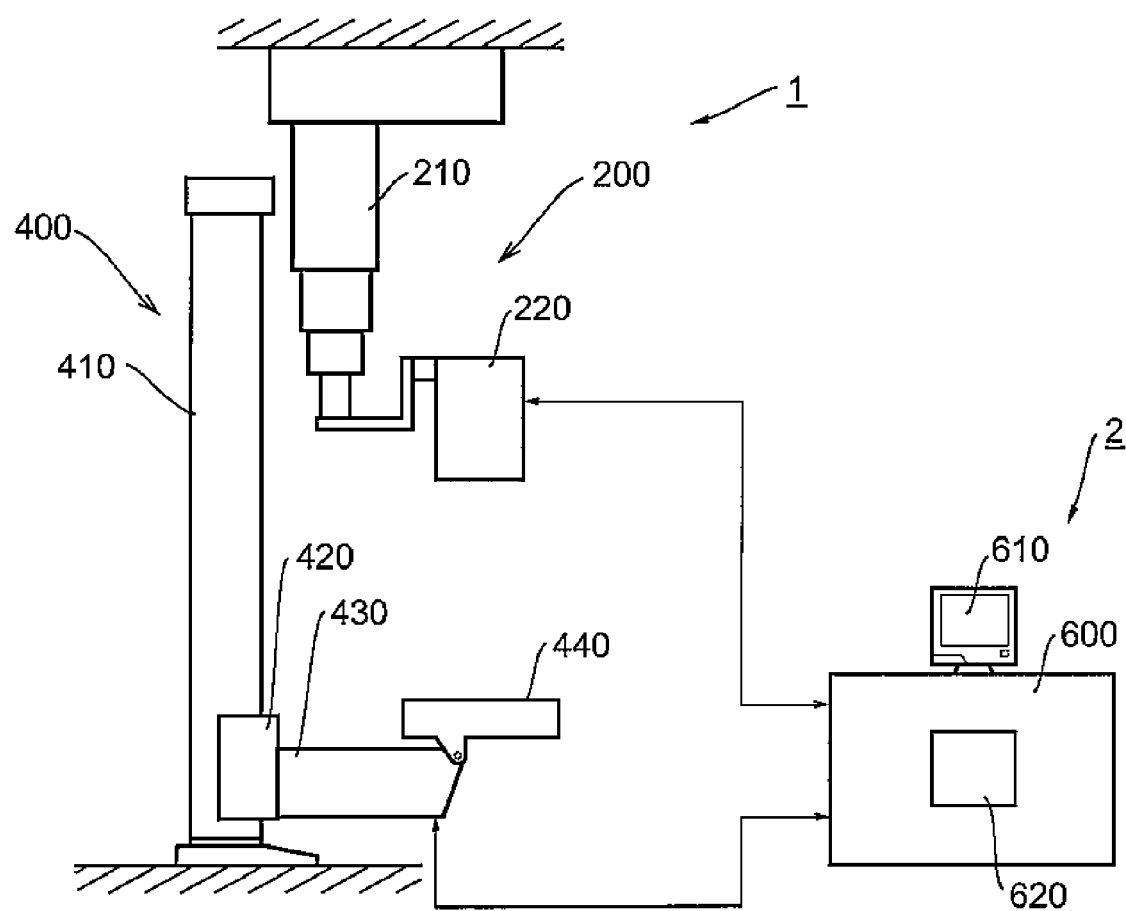
FIG. 1 is a diagram showing the configuration of an example of the best mode embodiment of the present invention.

As shown in FIG. 1, The apparatus 1 has an X-ray irradiation apparatus 200 and an X-ray detector 400. The X-ray irradiation apparatus 200 is composed of a column 210 suspended from the ceiling and an X-ray irradiator 220 attached the end of it. The X-ray irradiator 220 is an example of the X-ray irradiator of the present invention.

The X-ray irradiator 220 is designed to change the irradiation direction by changing its direction. The column 210 supporting the X-ray irradiator 220 is vertically extendable and horizontally movable.

An X-ray detection apparatus 400 is comprised of a column 410 perpendicular to the floor, a carriage 420 mounted to the column movably up and down, an arm 430 attached to carriage horizontally, and an X-ray detector 440 mounted at the end of the arm 430. This makes the X-ray detection apparatus 400 a wall-stand type X-ray detection apparatus.

The X-ray detector 440 is of flat structure and can change its X-ray incidence plane horizontally or vertically according to X-ray incidence direction. The X-ray detector 440 is an example of the X-ray detector of the present invention.

A detection signal from the X-ray detector 440 is input to an operator console 600. The operator console 600 reconstructs a fluoroscopic image of the subject based on the input signal from the X-ray detector and then displays on a display 610.

The operator console 600 controls the X-ray irradiation apparatus 200 and the X-ray detection apparatus 400 through the operator. The X-ray irradiation apparatus 200 controls not only the horizontal or vertical position and X-ray irradiation direction but also the intensity and irradiation timing of X-rays. The X-ray detection apparatus 400 controls the height of the X-ray detector 440 according to the X-ray irradiator 220 and also controls the direction of the X-ray incidence plane horizontally or vertically according to the X-ray incidence direction.

Figure 2:
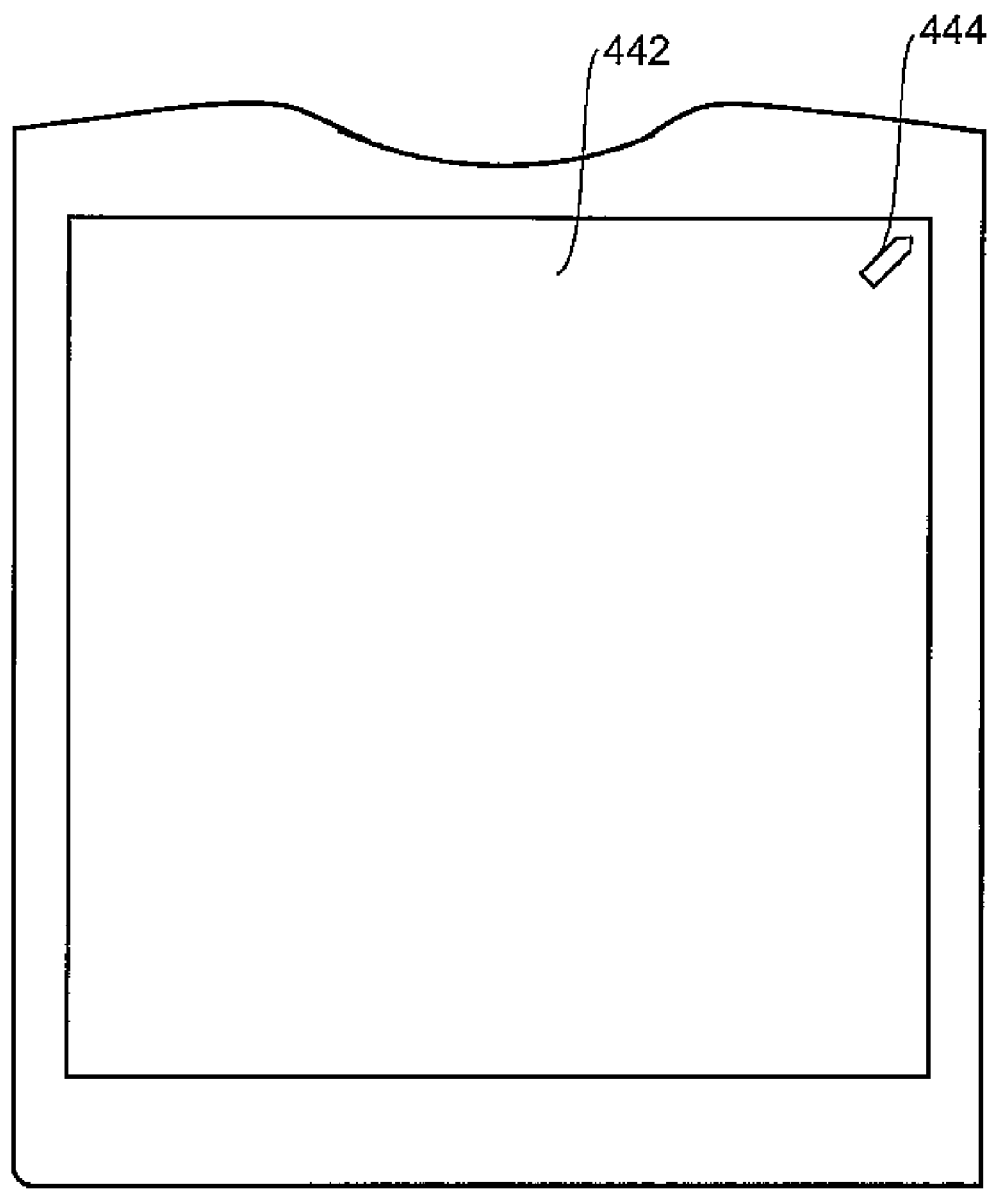
FIG. 2 is a diagram showing the front of an X-ray detector.

FIG. 2 is a front view of the X-ray detector. As shown in FIG. 2, the X-ray detector 440 has an X-ray incidence plane 442. The X-ray incidence plane 442 is a square plane coated with X-ray permeable protection film. An indicator 444 is printed at the upper right corner of the protection film. The indicator 444 is printed with X-ray permeable ink or paint.

Location of the indicator 444 is not limited but may be located at any corner (upper left, lower right, or lower left) of the X-ray incidence plane. This prevent the subject from being blocked when taking an image and thus the operator can view the image easily. The following description is in the case where the indicator is located at upper right corner, but the same is true for other locations.

Figure 3:
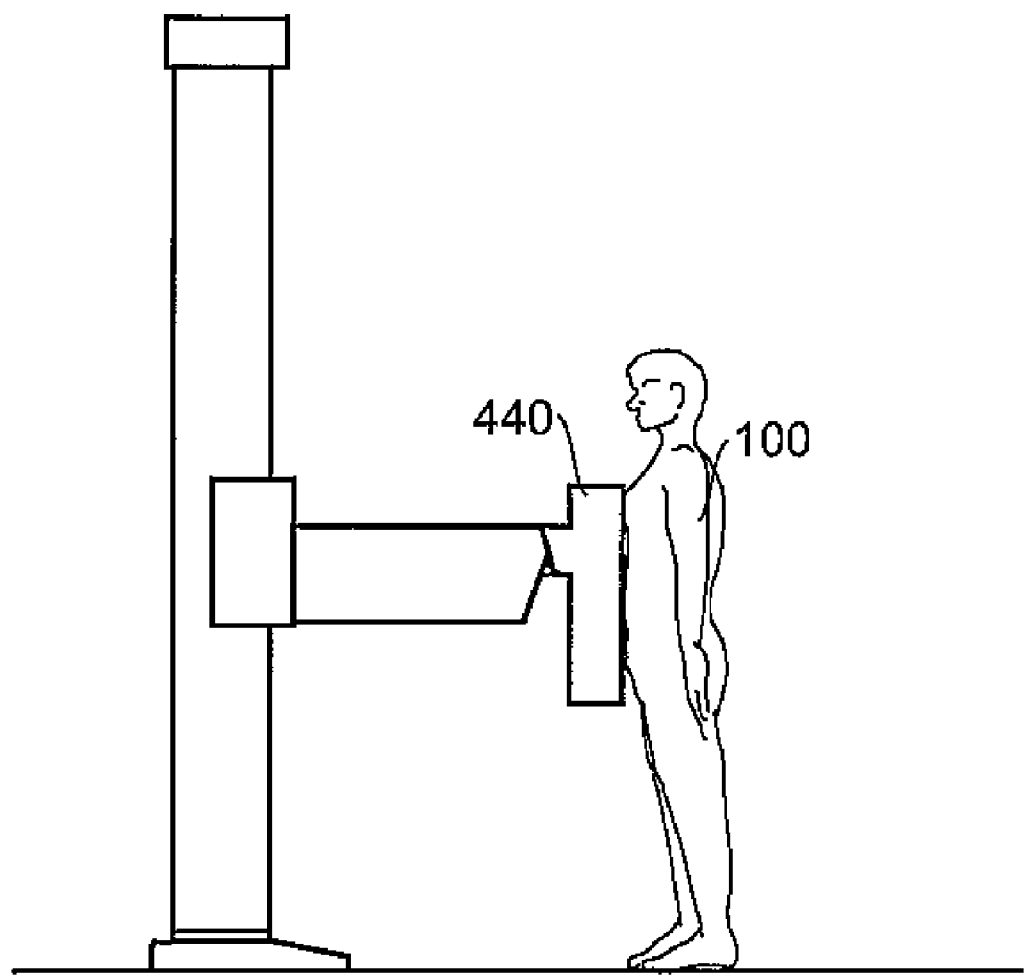
FIG. 3 is a diagram showing an example of taking an image.

FIG. 3 shows an example of taking an image. As shown in FIG. 3, a subject 100 in this embodiment is a human body which is standing with the venter facing the X-ray detector 440 and an X-ray is irradiated from its back. Here, an approximately line symmetrical fluoroscopic image about the body axis is taken. The X-ray irradiator 220 is not shown.

Figure 4:
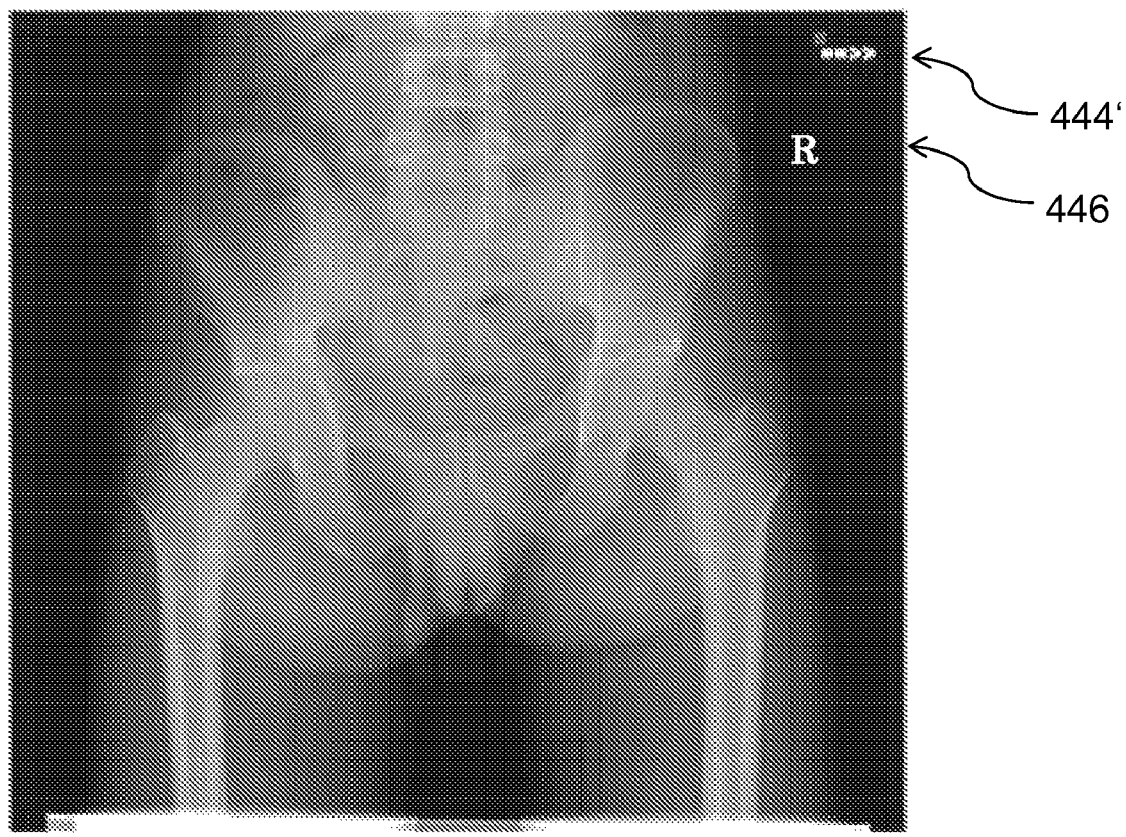
FIG. 4 is a photograph showing an example of gradation display of a fluoroscopic image.

As a result of this, a fluoroscopic image as shown in FIG. 4 is displayed on a display 610, for example. The display 610 is an example of the display device of the present invention. As shown in FIG. 4, a fluoroscopic image of the approximately horizontally symmetrical pelvis is displayed on the display 610. Also, an orient mark 444' is displayed at the upper right corner of the display screen. The orient mark 444' corresponds to the indicator 444 on the X-ray incidence plane 442.

The orient mark 444' is generated by the operator console 600 and overlaid on the fluoroscopic image. Since location of the indicator 444 on the X-ray incidence plane 442 is predetermined, for example, at upper right corner and the operator console 600 displays the orient mark at the upper right corner of the screen accordingly.

On the right side of such a fluoroscopic image, a postural mark (a mark indicating the direction of the subject) 446 is written by the operator. Writing of the postural mark 446 is performed through a writing section 620 included in the operator console 600. The fluoroscopic image display apparatus 2 of the present invention includes the display 610 and the writing section 620.

The postural mark 446 in this case is "R". "R" device "right". Since an image is taken by irradiating an X-ray from the back, it is evident that the side where the orient mark 444' is displayed is right. Therefore, the operator writes "R" on the orient mark 444' side.

Because of this writing, the left and right of the fluoroscopic image can be distinguished. The fluoroscopic image is stored with "R" written. This makes it possible to interpret a radiogram with left and right shown clearly at the time of later interpretation.

Figure 5:
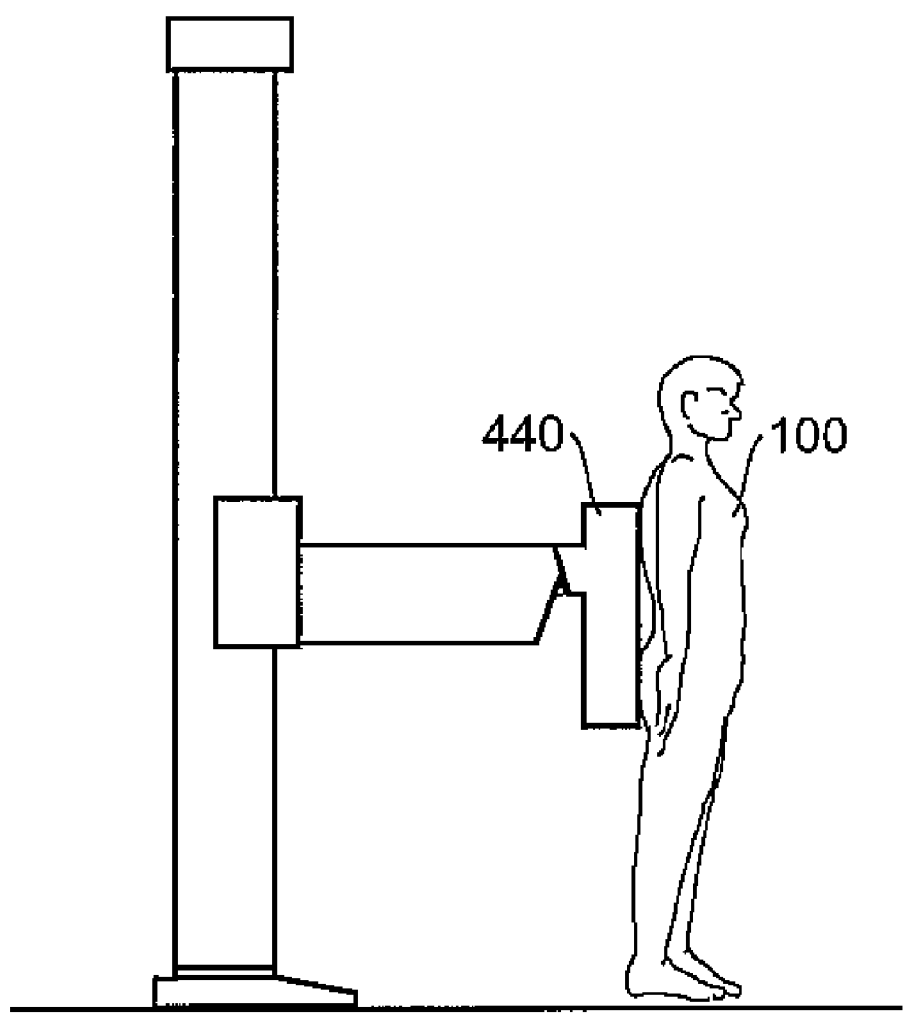
FIG. 5 is a diagram showing an example of taking an image.

FIG. 5 shows another example of taking an image. As shown in FIG. 5, a subject 100 is standing with the back facing the X-ray detector 440 and an X-ray is irradiated from the belly side. The X-ray irradiator 220 is not shown.

Figure 6:
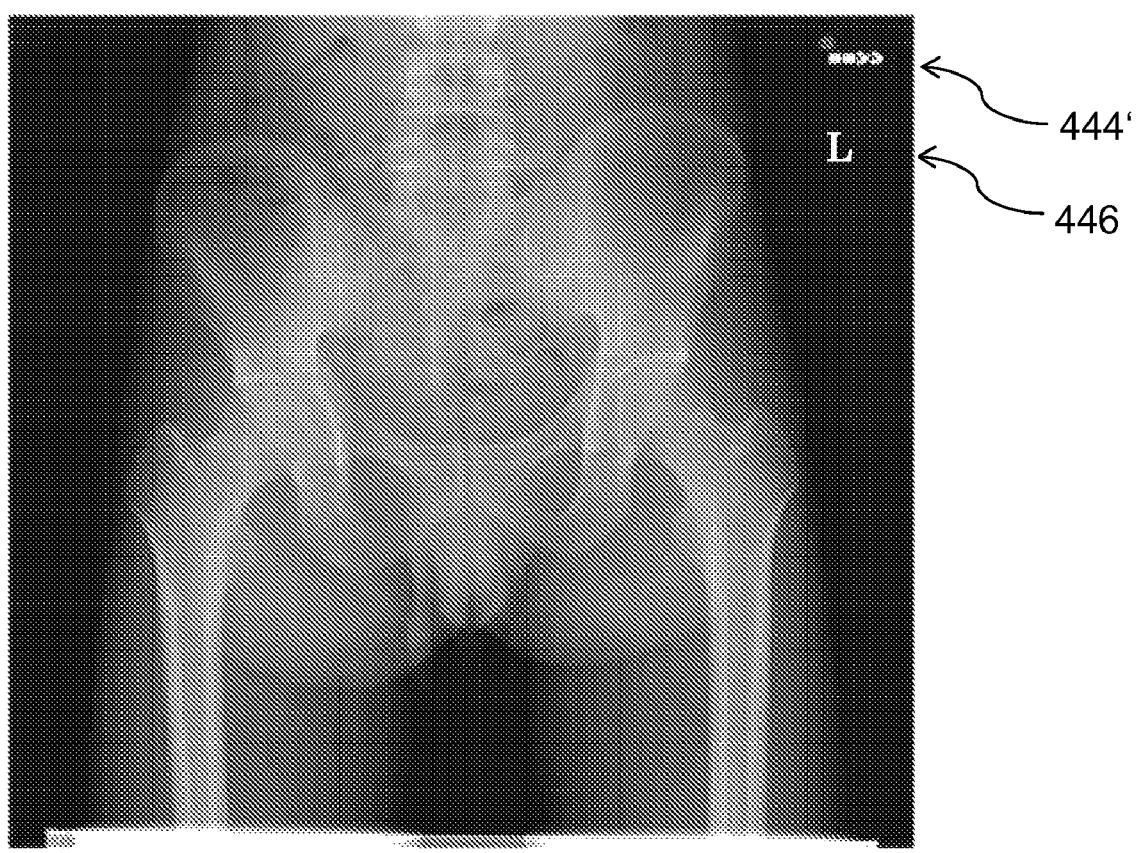
FIG. 6 is a photograph showing an example of gradation display of a fluoroscopic image.

As a result, a fluoroscopic image as shown in FIG. 6 is displayed on the display 610, for example. The display 610 is an example of the display device of the present invention. As shown in FIG. 6, a fluoroscopic image of the pelvis is displayed on the display 610. Also, the orient mark 444' is displayed at the upper right corner of the screen. The orient mark 444' corresponds to the indicator 444 on the X-ray incidence plane 442.

The orient mark 444' is generated by the operator console and overlaid on the fluoroscopic image. Since location of the indicator 444 on the X-ray incidence plane 442 is predetermined, for example, at the upper right corner, the operator console 600 displays the orient mark 444' at the upper right corner of the screen accordingly.

On the right side of such a fluoroscopic image, the postural mark 446 is written. Writing of the postural mark 446 is performed through the operator console 600. The operator console 600 is an example of the writing device of the present invention.

The postural mark 446 in this case is "L". "L" device "left". Since an image is taken by irradiating an X-ray from the belly side, it is evident that the side where the orient mark 444 is displayed is left. Therefore, the operator writes "L" on the orient mark 444' side.

As a result of this writing, the left and right of a fluoroscopic image can be distinguished. The fluoroscopic image is stored with a mark "L" written. This makes it possible to interpret a radiogram with left and right clearly shown at the time of later interpretation.

Figure 7:
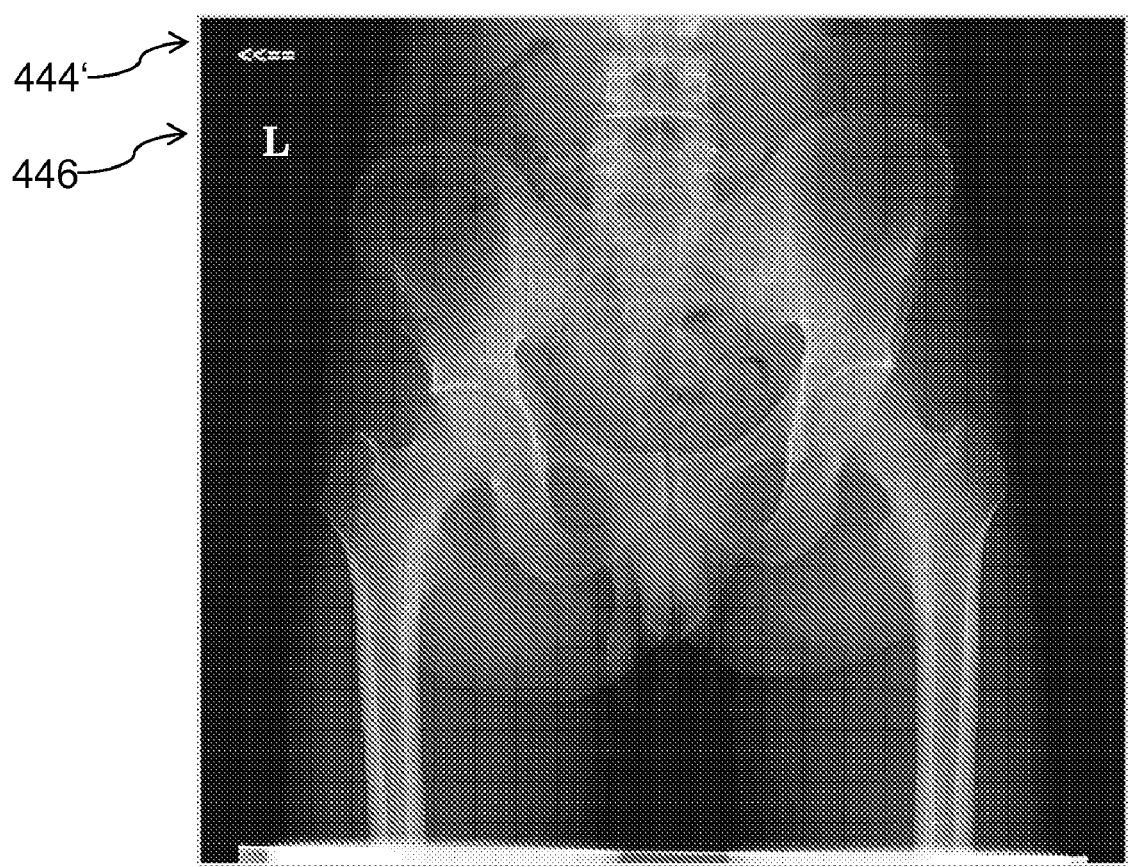
FIG. 7 is a photograph showing an example of gradation display of a fluoroscopic image.

As shown in FIG. 7, when a fluoroscopic image taken by irradiating an X-ray from the front is displayed reversely, i.e. an image taken from the back is displayed, an image with the orient mark 444' displayed at the upper left corner is obtained. Even in such a case, it is evident that the side where the orient mark 444' is displayed is left, and therefore the operator writes "L" on the orient mark 444' side. In contrast, when a fluoroscopic image taken by irradiating an X-ray from the back is displayed reversely, the operator writes "R" on the orient mark 444' side.

Figure 8:
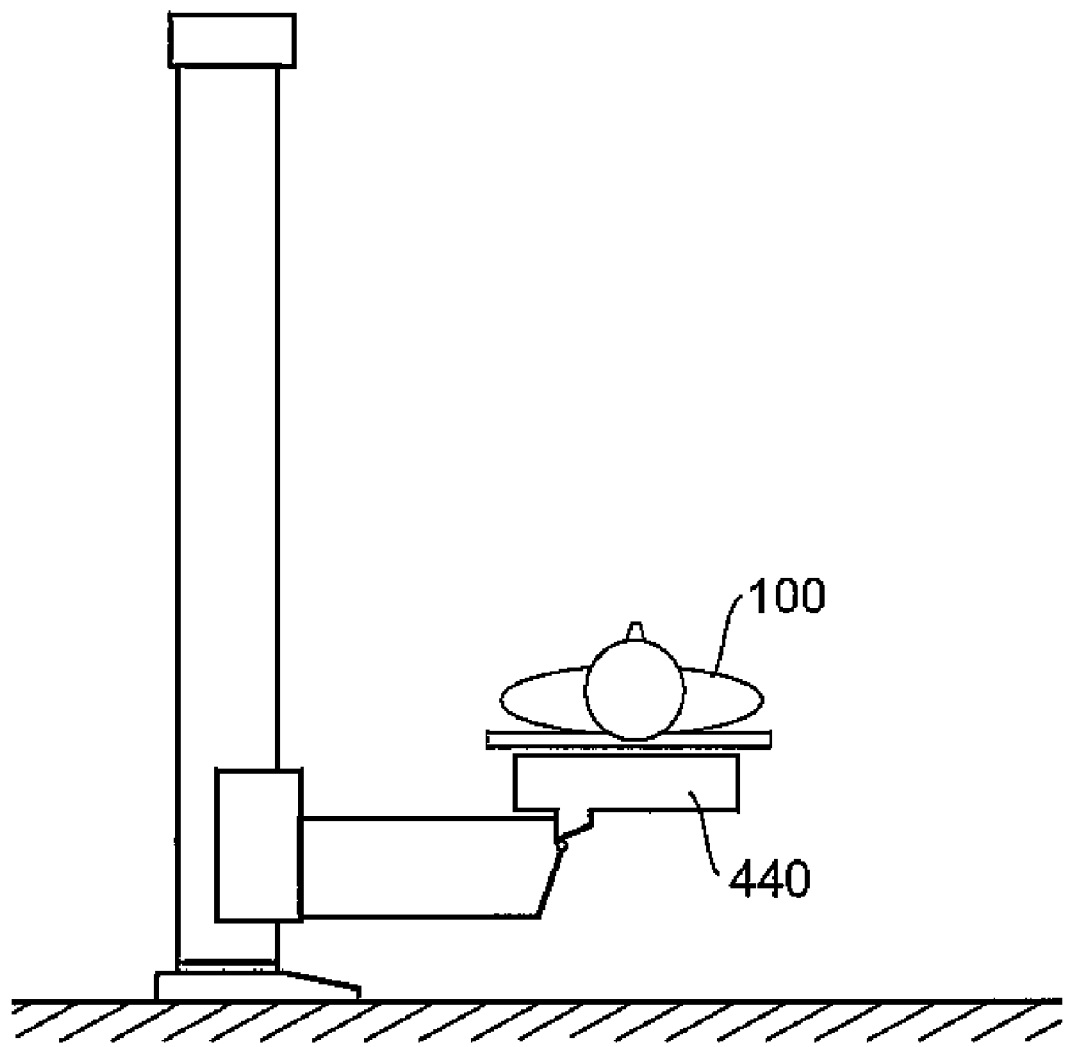
FIG. 8 is a diagram showing an example of taking an image.

FIG. 8 shows still another example of taking a fluoroscopic image. As shown in FIG. 8, the subject 100 is lying with the back facing the X-ray detector 440 and the head facing upward, and an X-ray is irradiated from the belly side. The X-ray irradiator is not shown.

Figure 9:
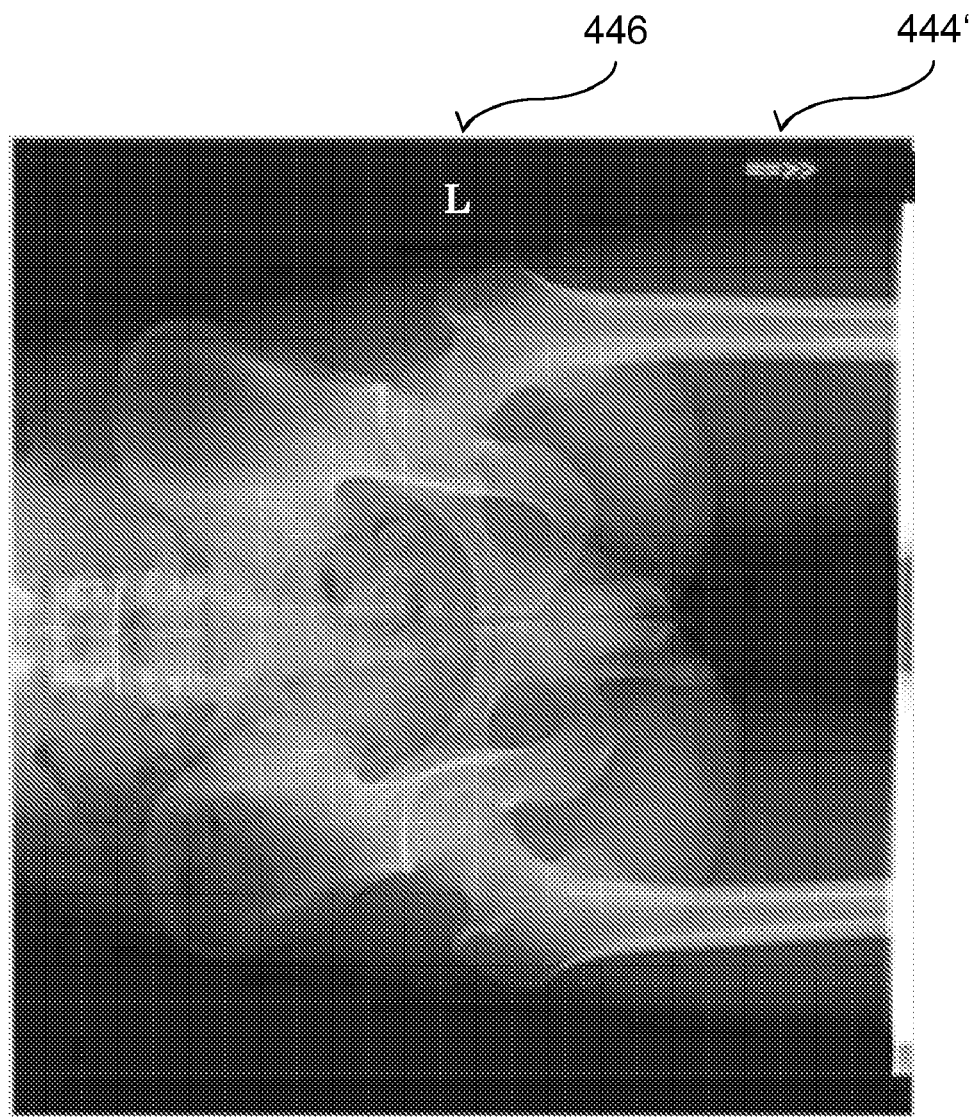
FIG. 9 is a photograph showing an example of gradation display of a fluoroscopic image.

As a result, a fluoroscopic image as shown in FIG. 9 is displayed on the display 610, for example. The display 610 is an example of the display device of the present invention. As shown in FIG. 9, a fluoroscopic image of the pelvis is displayed on the display 610. Also, the orient mark 444' is displayed at the upper right corner of the screen. The orient mark 444' corresponds to the indicator 444 on the X-ray incidence plane 442.

The orient mark 444' is generated by the operator console 600 and overlaid on the fluoroscopic image. Since the location of the indicator 444 on the X-ray incidence plane 442 is predetermined, for example, at the upper right corner, the operator console 600 displays the orient mark 444' at the upper right corner of the screen.

On the top of such a fluoroscopic image, the operator writes the postural mark (a mark indicating the direction of the subject) 446. Writing of the postural mark 446 is performed through the operator console 600. The operator console 600 is an example of the writing device of the present invention.

The postural mark 446 in this case is "L". "L" device "left". Since the subject is lying and an X-ray is irradiated from the belly side with the back facing the X-ray detector and the head facing upward, it is evident that the side where the orient mark 444' is displayed is left. Therefore, the operator writes "L" on the orient mark 444' side. The same is true in the case where the subject is lying and X-ray is irradiated with the belly side facing the X-ray detector 440 and the head downward.

This clarifies the left and right of a fluoroscopic image. The fluoroscopic image is stored with "L" written. Therefore, it is possible to interpret a radiogram with left and right clarified at the time of later interpretation.

When an X-ray is irradiated when the subject is lying and with the belly side of a subject facing the X-ray detector 440 and the head facing upward, it is evident the side where the orient mark 444' is displayed is right. In this case, "R" is written as the postural mark. The same is true in the case where an X-ray is irradiated from the belly side when the subject is lying and with the back of the subject facing the X-ray detector 440 and the head facing downward.

What is claimed is:

1. An X-ray imaging apparatus comprising:
   an X-ray irradiator configured to irradiate a subject using X-rays;
   an X-ray detector configured to detect the X-rays that pass through the subject, said X-ray detector comprising a visible indicator at an end of an X-ray incidence plane as a positional standard on the X-ray incidence plane; and
   a display device configured to display a fluoroscopic image based on the detection signals from said X-ray detector together with an orient mark corresponding to a position of the indicator.

2. An X-ray imaging apparatus according to claim 1, wherein:
   the indicator is positioned on either side of an approximately line symmetrical subject; and
   said display device is configured to display the orient mark on a side corresponding to the indicator to form a symmetrical fluoroscopic image of the approximately line symmetrical subject.

3. An X-ray imaging apparatus according to claim 2, wherein said display device is configured to display the orient mark on one of a left side of the subject and a right side of the subject.

4. An X-ray imaging apparatus according to claim 1, further comprising a writing device configured to enable a mark indicating the direction of the subject to be written on the fluoroscopic image displayed by said display device.

5. An X-ray imaging apparatus according to claim 4, wherein:
   the indicator is positioned on either side of an approximately line symmetrical subject;
   said display device is configured to display the orient mark on the side corresponding to the indicator for the approximately line symmetrical subject; and
   said writing device is configured to enable the mark indicating the direction of the subject to be written on the same side as the orient mark.

6. An X-ray imaging apparatus according to claim 5, wherein said display device is configured to display the orient mark on one of a left side of the subject and a right side of the subject, and said writing device is configured to enable the mark indicating whether the direction of the subject is right or left to be written on the same side as the orient mark.

7. An X-ray imaging apparatus according to claim 1, wherein the indicator is permeable to X-rays.

8. An X-ray imaging apparatus according to claim 1, wherein said display device is configured to enable the fluoroscopic image to be displayed reversely by at least one of rotating and flipping the fluoroscopic image.

9. An X-ray imaging apparatus according to claim 8, wherein said display device is configured to display the indicator in a constant direction.

10. An X-ray imaging apparatus according to claim 8, wherein said display device is configured to display the orient mark in a constant direction.

11. A fluoroscopic image display apparatus comprising:
a display device configured to display a fluoroscopic image together with an orient mark that corresponds to a visible indicator as a positional standard on an X-ray incidence plane and is provided at an end of the X-ray incidence plane of an X-ray detector used for taking the fluoroscopic image.

12. A fluoroscopic image display apparatus according to claim 11, wherein said display device is configured to display the orient mark together with a symmetrical fluoroscopic image of an approximately line symmetrical subject on a side corresponding to the indicator.

13. A fluoroscopic image display apparatus according to claim 12, wherein said display device is configured to display the orient mark on one of a left side of the subject and a right side of the subject.

14. A fluoroscopic image display apparatus according to claim 11, further comprising a writing device configured to enable a mark indicating a direction of the subject to be written on the fluoroscopic image displayed by said display device.

15. A fluoroscopic image display apparatus according to claim 14, wherein:
said display device is configured to display the orient mark together with a symmetrical fluoroscopic image of an approximately line symmetrical subject on a first side corresponding to the indicator; and
said writing device is configured to enable the mark indicating the direction of the subject to be written on the first side.

16. A fluoroscopic image display apparatus according to claim 15, wherein:
said display device is configured to display the orient mark on one of a left side of the subject and a right side of the subject; and
said writing device is configured to enable a mark indicating whether the direction of the subject is right or left to be written on the same side as the orient mark.

17. A fluoroscopic image display apparatus according to claim 11, wherein said display device is configured to change a direction of the fluoroscopic image by at least one of rotating and reversing the fluoroscopic image.

18. A fluoroscopic image display apparatus according to claim 17, wherein said display apparatus is configured to display the indicator in a constant direction.

19. A fluoroscopic image display apparatus according to claim 17, wherein said display apparatus is configured to display the orient mark in a constant direction.

20. An X-ray imaging method comprising:
irradiating a subject with X-rays emitted by an X-ray irradiator;
detecting X-rays that pass through the subject using an X-ray detector having a visible indicator at an end of an X-ray incidence plane as a positional standard on the X-ray incidence plane; and
displaying a fluoroscopic image and an orient mark on a display device, the fluoroscopic image based on detection signals from the X-ray detector, the orient mark corresponding to a position of an indicator.

* * * * *